United States Patent [19]
Shukla et al.

[11] Patent Number: 6,103,195
[45] Date of Patent: Aug. 15, 2000

[54] MICRO-VOLUME SPIN COLUMNS FOR SAMPLE PREPARATION

[76] Inventors: Ashok K. Shukla; Amita Shukla; Mukta Shukla, all of 10423 Popkins Ct., Woodstock, Md. 21163

[21] Appl. No.: 08/908,931

[22] Filed: Aug. 8, 1997

[51] Int. Cl.[7] .................................................. G01N 30/02
[52] U.S. Cl. ...................... 422/70; 210/198.2; 210/657; 422/69; 422/72; 422/101; 422/102
[58] Field of Search ................................. 422/69, 70, 72, 422/101, 102; 210/198.2, 657

[56] References Cited

U.S. PATENT DOCUMENTS

| | | | |
|---|---|---|---|
| 3,539,300 | 11/1970 | Stone . | |
| 4,787,971 | 11/1988 | Donald | 210/198.2 |
| 4,871,675 | 10/1989 | Coupek et al. | 422/102 |
| 4,892,710 | 1/1990 | Wong et al. | 422/102 |
| 5,057,426 | 10/1991 | Henco et al. . | |
| 5,336,412 | 8/1994 | Huse et al. | 210/635 |
| 5,438,128 | 8/1995 | Nieuwkerk et al. | 536/25.4 |
| 5,496,473 | 3/1996 | Chow | 210/635 |

*Primary Examiner*—Jan Ludlow

[57] ABSTRACT

This invention relates to micro volume spin columns used for the preparation and purification of small chemical and/or biological samples by centrifugation. The present invention relates to the use of the conventional luer lock fitting in micro volume spin columns. This invention also relates to multi-spin column systems based on joining two or more spin columns by their ends or by combining different filtration or ultra-filtration membranes with spin columns.

14 Claims, 7 Drawing Sheets

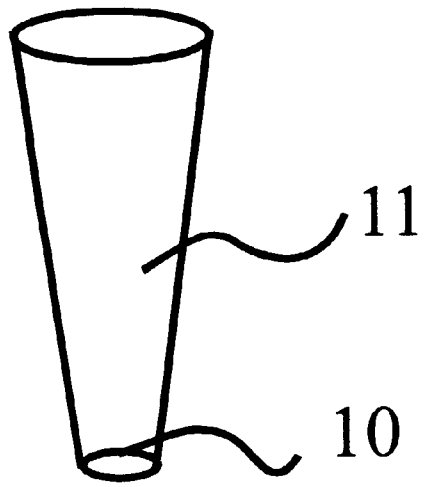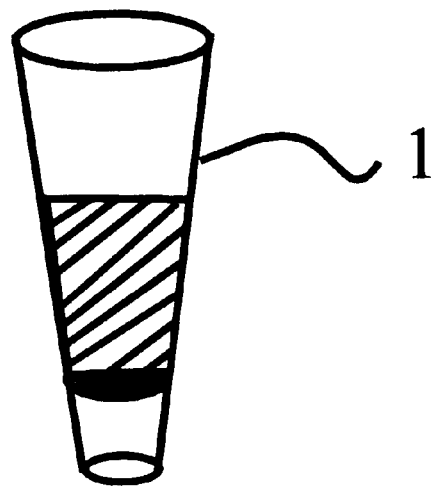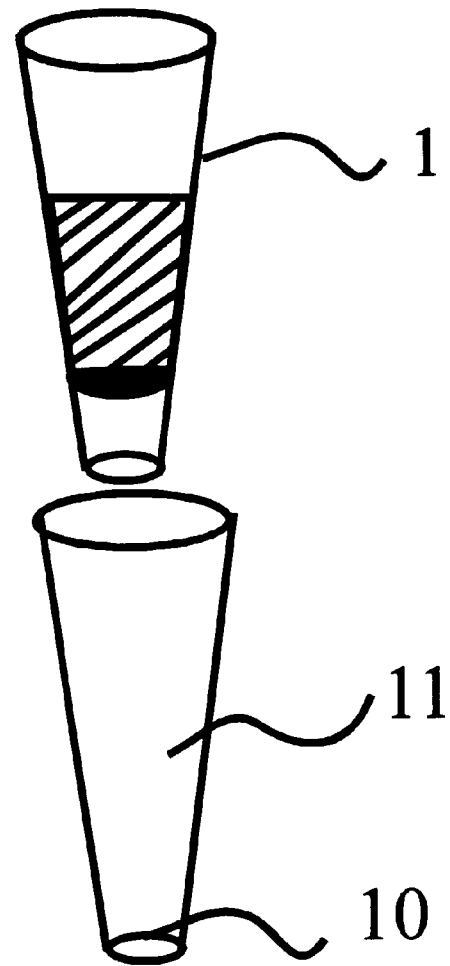
Fig. 5a Fig. 5b
Fig. 5

MICRO-VOLUME SPIN COLUMNS FOR SAMPLE PREPARATION

FIELD OF THE INVENTION

This invention relates to micro volume spin columns used for the preparation and purification of small chemical and/or biological samples by centrifugation. The present invention relates to the use of the conventional luer lock fitting in micro volume spin columns. This invention also relates to multi-spin column systems based on joining two or more spin columns by their ends or by combining different filtration and ultra-filtration membranes with spin columns.

BACKGROUND OF THE INVENTION

The purification of small biological and chemical samples has become increasingly common in biotechnological and biomedical research. Due to the high numbers of small sample volumes, many highly sensitive analytical methods have been developed. A number of methods such as dialysis, spinning samples through filtration membranes or using spin columns filled with different absorption materials, are among the most common techniques for purifying and separating small sample volumes.

Spin columns are small columns that purify and/or separate the components of a sample by centrifugation. The columns are made of a tube in which solid column material is held in place by a filter or fritte at the base of the column. The sample is introduced at the top of the column and centrifugation results in the purification or component alteration of the sample as it passes through the solid matrix. Through this method, undesired molecules can be removed from a sample by using adsorption gel filtration, ion-exchange, affinity separation and similar methods.

Currently, many different types of spin columns with different fittings at their ends, are available in the market. However, there are no spin columns with uniform fittings currently available in the market so that, the columns can not be securely interconnected or joined together with other columns to allow versatility in the preparation and purification of samples. This method allows a combination of different columns for one-step purification.

The present invention describes the use of standard luer fittings at the top and the bottom of spin columns. The two types of luer fittings, screw and slide-in, both create secure and strong seals when two luer fittings are joined together.

One of the main advantages of luer fittings is that multiple columns can be attached to each other for the one-step purification of samples. This process will lead to faster sample preparation since a sample can directly move from the bottom of one column to the top of the next column. Furthermore, sample loss is minimized since a sample does not need to be transferred from one column system into another column system for each purification or sample separation step.

SUMMARY OF THE INVENTION

It is an object of this invention to provide fast, specific, efficient and loss-minimizing small sample preparation and purification.

It is a further object of this invention to provide standard, easy-to-use fittings, for combining different spin columns.

It is a further object of this invention to combine sample dialysis with spin column-based technology for further sample purification.

The various features of novelty that characterize the present invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments from study of the following drawings, in which:

FIGS. 5a and 5b show a luer fitting with a dialysis membrane joined to a spin column.

DESCRIPTION OF THE PREFERRED EMBODIMENTS

Figure 1:
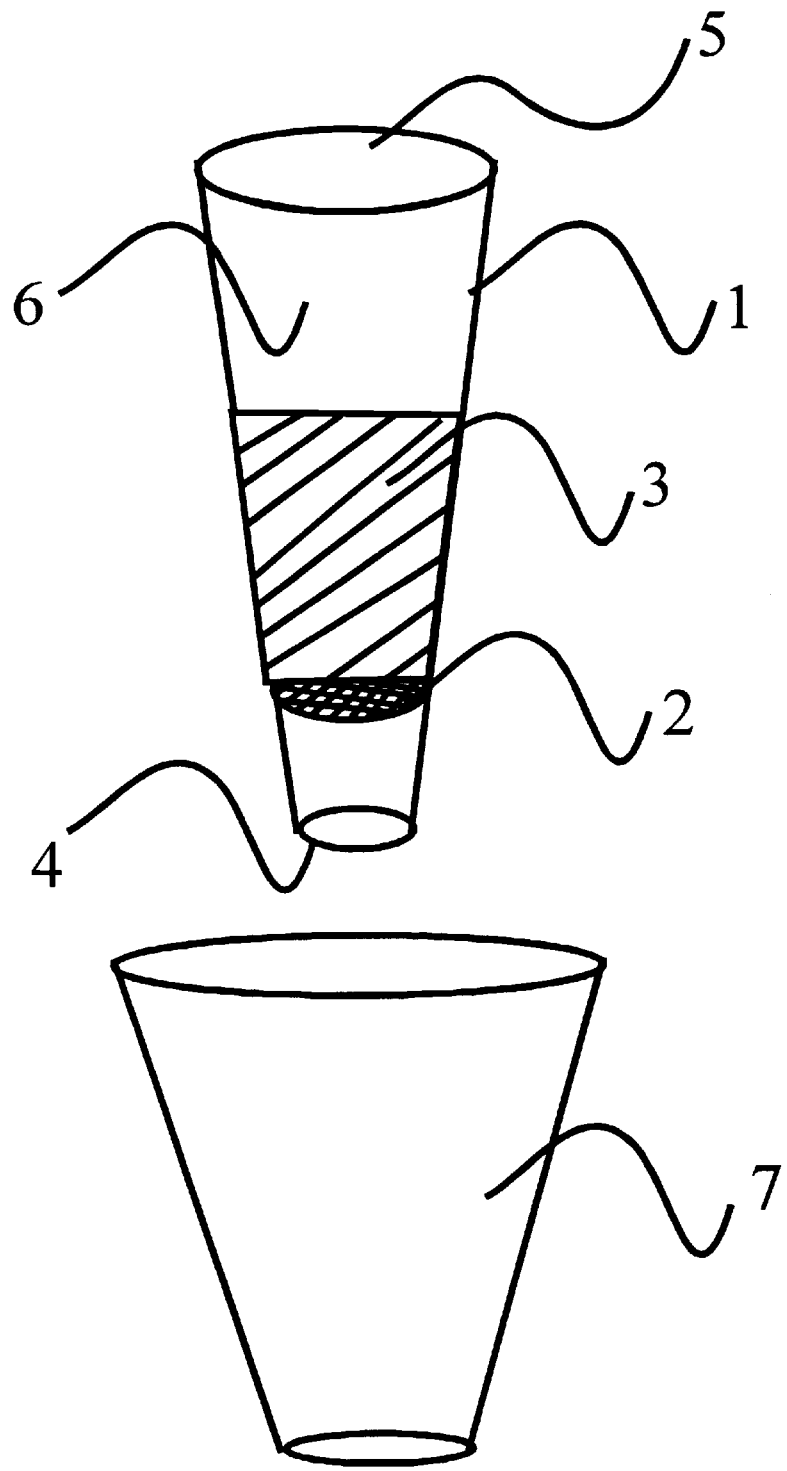
FIG. 1 is a view of a spin column.
Figure 6:
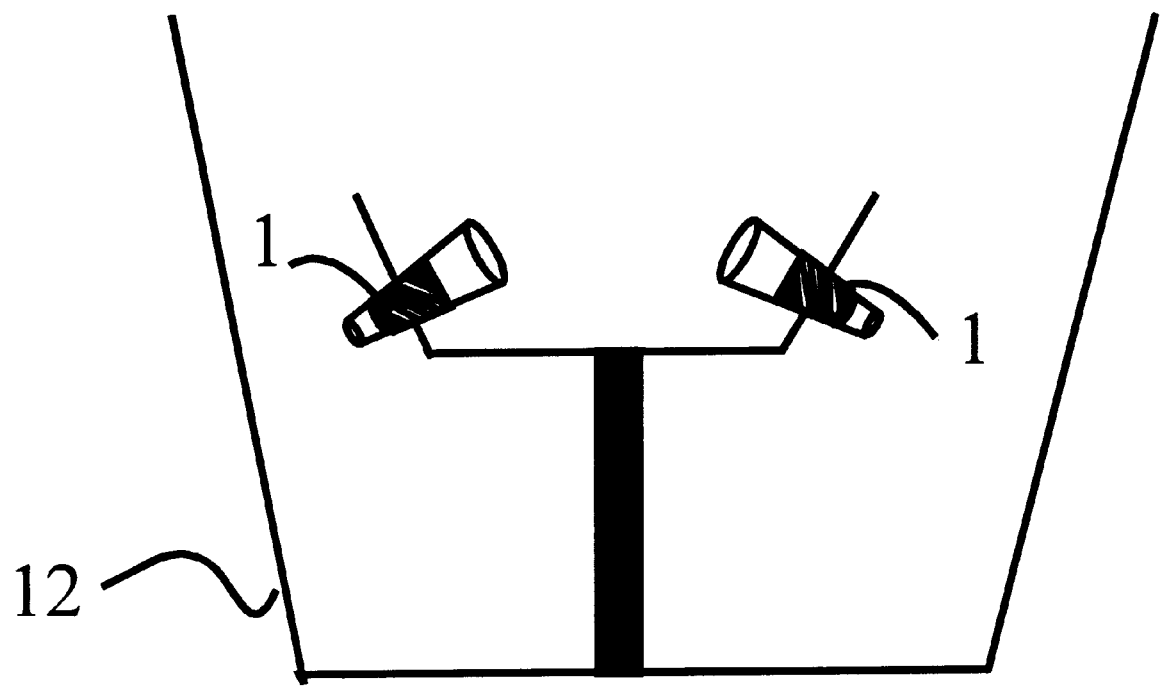
FIG. 6 shows spin columns placed in a centrifuge.

Referring to the drawings, FIG. 1 shows a micro volume spin column (1), which has a male luer fitting (4) at the bottom and a female luer fitting (5) at the top. The column (1) also contain a filter (2) that holds the solid filling material (3) in the column. The filter (2) can either be a fritte or it can be composed of a membrane. The sample is introduced in the sample chamber (6). When the spin column is placed in a centrifuge (12), as shown in FIG. 6, the sample molecules selectively pass through the column material (3). While the solid matrix is retained in the column by the filter (2) and certain sample molecules are entrapped in the matrix, other sample molecules pass through the filter into the collection vial (7).

The micro volume spin column (1) can be made of materials such as plastic or Teflon or any other inert materials that do not react with the mobile elution phase or the chemical and/or biochemical compounds used for sample preparation. The filter (2) can also be made of any inert material.

Figure 3A:
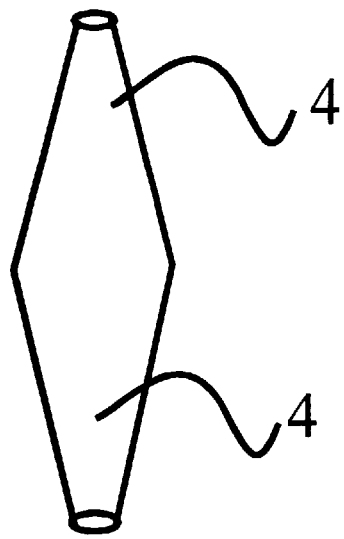
FIGS. 3a, 3b, 3c, 3d and 3e are view of spin columns with different types of luer fittings at each of the ends.
Figure 3B:
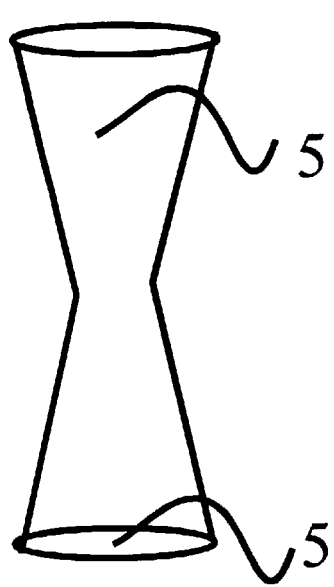
Figure 3C:
Figure 3D:
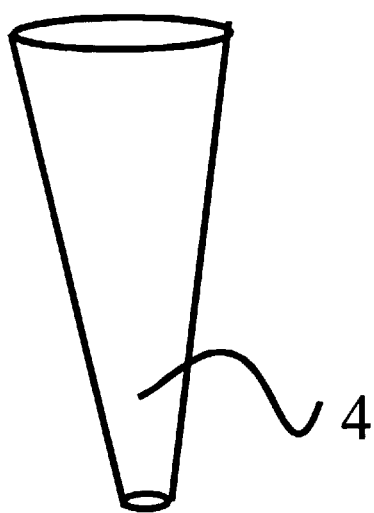
Figure 3E:
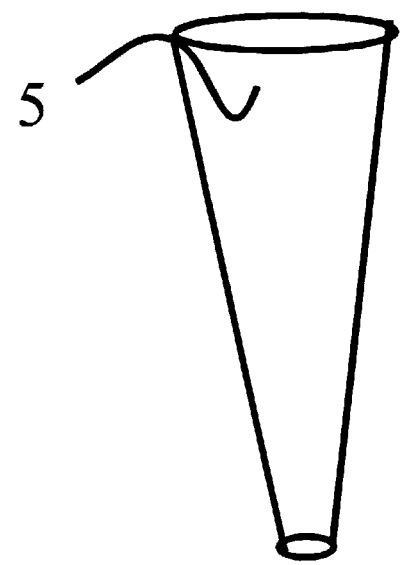

The leur fittings (4, 5) are present at one or both ends of the spin column, as shown in FIGS. 3a–3e. A spin column can have either two male fittings (FIG. 3a) two female fittings (FIG. 3b) or one male and one female fitting (FIG. 3c). Spin columns with only one luer fitting can have either one male fitting (FIG. 3d) or one female fitting.

Figure 2A:
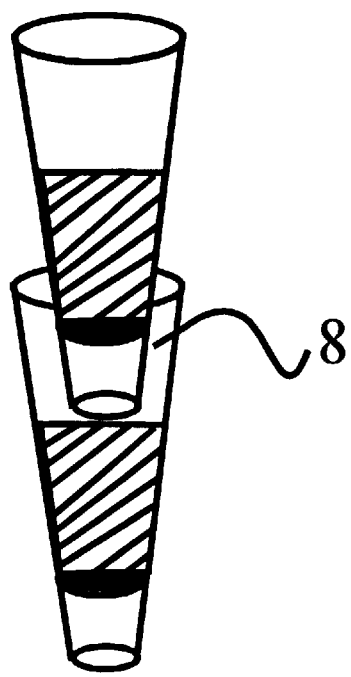
FIGS. 2a, 2b, 2c and 2d are a view of multiple spin columns joined through luer fittings.
Figure 2B:
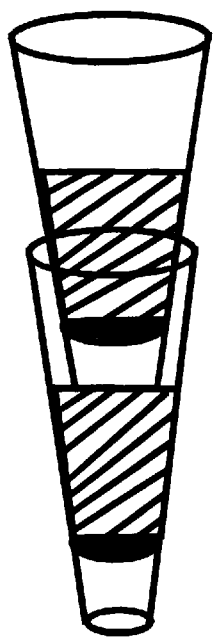
Figure 2C:
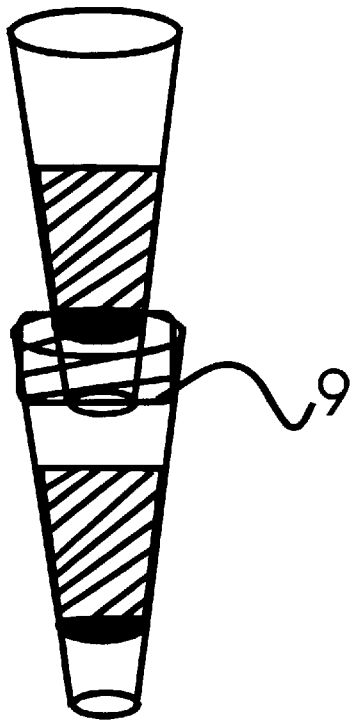

Joining a male luer fitting (4) to a female luer fitting (5), as shown in FIG. 2a, can combine different spin columns at the ends. The joint made between the two fittings can either be a slide-in luer joint (8) as shown in FIG. 2b, or a screw-in luer joint (9) as shown in FIG. 2c.

Figure 2D:
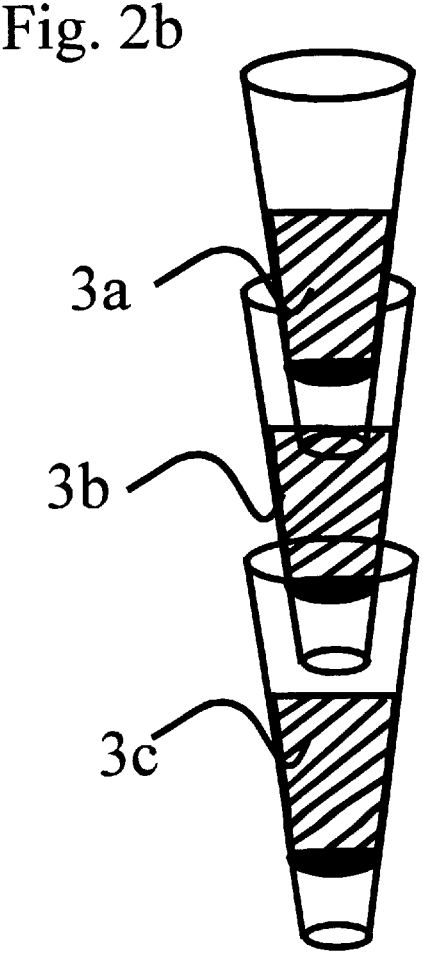

By using any combination of the different types of spin columns shown in FIGS. 2a–2d, two or more spin columns can be combined, as shown in FIG. 2d. Each of the spin columns shown in FIG. 2d can contain different column materials, such as solid and/or liquid matrix materials, (3a, 3b, 3c) or the same material.

Figure 4:
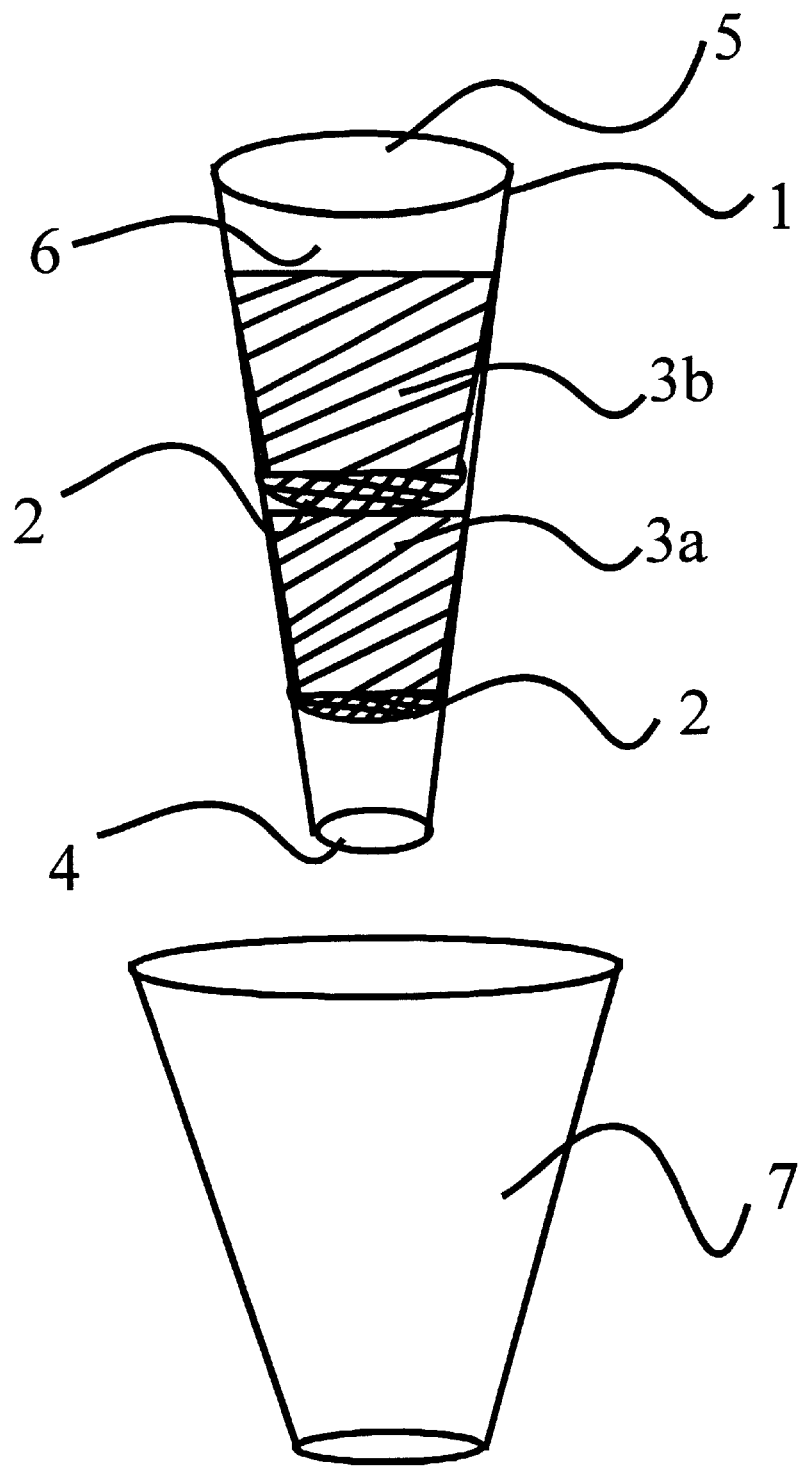
FIG. 4 shows spin columns containing two or more different types of column materials.

FIG. 4 shows spin columns with two or more different column materials placed in them. As can be seen in FIG. 4a, the first type of solid column material (3a) is separated from the second type of solid column material (3b) by a filter (2).

In addition to sample purification and preparation through spin columns, dialysis can be also performed with the spin columns to further separate the sample. By using dialysis the dissolved molecules can be selectively purified since membranes with different molecular weight cut offs allow only selective dissolved molecules to pass through. As shown in FIG. 5a, a sample can be placed in a column (11) which has a membrane (10) of a specified molecular weight cutoff (MWCO) placed at the bottom. When the sample is placed inside the column (11), during centrifugation the sample first passes through the membrane such that only molecules of the desired MWCO enter the spin column (1). The sample is then separated in the spin column. Alternately, as shown in FIG. 5b, the sample can first pass through one or more spin columns (1) and then enter a column (11) with a membrane (10) placed in it. Both of the combinations shown in FIGS. 5a and 5b result in selective sample purification and/or separation through the spin column and also separate or filter the sample on the basis of molecular weight through dialysis. For instance, the simultaneous use of an ion-exchange matrix and a selected membrane can purify a sample very selectively. By using two or more membranes this selectivity can be further enhanced due to the different properties of the membranes.

Furthermore, the use of a membrane (10), as shown in FIGS. 5a and 5b, can enhance separation through a spin column (1) since the flow of the sample through the membrane (10) is slower during centrifugation than it would be without the membrane due to flow resistance. Controlling the flow rate of the sample into the sample chamber (6) and subsequently the solid matrix (3) thus results in enhanced and increased interactions between the sample and the column material (3) leading to better sample separation and/or purification.

Figure 7:
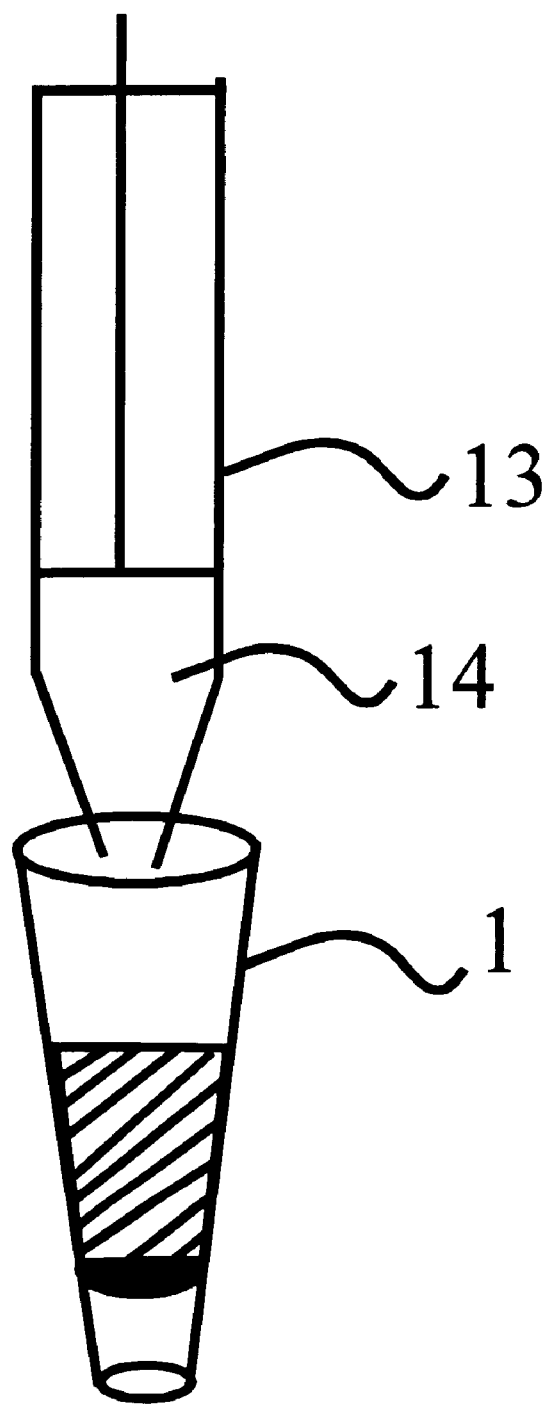
FIG. 7 shows the use of the spin column with a syringe.

As shown in FIG. 7, a syringe (13) with luer fittings can be attached to the top end of a column or multi-columns. In this way, the sample (14) can be purified and or separated by being applied to the columns through the syringe. This method eliminates the need for centrifugation.

The broader usefulness of the invention may be illustrated by the following examples.

EXAMPLES OF APPLICATIONS

Example 1

Sample Separation Using Spin Column

A spin column containing (about 100 ul) G-50 sephadex gel filtration material in distilled water is first spun in a 1.5 ml microfuge tube at 3000 g for 3 minutes to remove excess water. Once the centrifugation is complete, a sample containing albumin, vitamin B12 and salt is placed in the sample chamber. When the spin column is centrifuged again, the G-50 material absorbs the smaller sample molecules such as salt and vitamin B12 (molecular weight 1300). The filtrate in the microfuge is analyzed by High Performance Liquid Chromatography (HPLC) and the results indicate that albumin is not retained by the column while both salt and vitamin B12 are no longer present in the separated sample.

Example 2

Using Two or More Spin Columns in Combination

Two or more spin column can be joined together at their ends as shown in FIG. 2. This enhances the specificity of the sample preparation process while simultaneously minimizing sample loss. For instance, selective separation of the sample containing albumin, vitamin B12 and salt can be achieved by using a column filled with the G-10 solid matrix (column A) in combination with a column containing G-50 solid matrix (column B). The bottom of column A is joined to the top of column B and the sample is placed in the sample chamber of column A. Since G-10 absorbs salt but not smaller molecules such as vitamin B12 the sample that emerges from column A and enters column B contains only vitamin B12 and albumin. Since column B traps both salt and vitamin B12, only albumin will flow out of the bottom of this column. By this method, the different components of the sample can be separated. The filtrates of each column are then analyzed by HPLC for purity.

Example 3

Using Spin Column with Membrane

As described in FIG. 5, if a column containing a membrane is placed on the top of the spin column such that the sample moves through the membrane prior to coming in contact with the column material, the quality of the separation is further improved. During centrifugation of the spin column, the presence of a membrane retards the speed at which the sample reaches the surface of the column material and moves through the solid matrix. This increases the interaction between the column material and the sample, consequently improving the quality of the separation.

Ion-exchange membranes can also be used for selective filtration.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A micro spin column with the following components:
   a. A solid matrix,
   b. luer fittings at one or both ends of the column,
   c. a porous filter, fritte, membrane or any other material used to keep the matrix in the column during centrifugation or vacuum application,
   d. a sample membrane located above the solid matrix, wherein said sample membrane is a dialysis membrane,
   e. a collecting tube, which collects the sample after it has moved through the column.

2. A spin column, as in claim 1, which can be made of any material.

3. A spin column, as in claim 1, where the solid matrix can be of any shape or size and can be made of any polymer or other materials.

4. A spin column, as in claim 1, where the solid matrix can be made of silica or be chemically or physically modified.

5. A spin column, as in claim 1, where the solid matrix can be composed of one or more solid matrices, which may or may not be made of different column materials and which are separated by porous filters, frittes or any other materials.

6. A spin column, as in claim 1, where the column has a liquid matrix.

7. A spin column, as in claim 1, where the column has membranes of one or more different types of pore sizes and/or Molecular Weight Cut Off's (MWCO) attached at one or both ends, where the porosity or molecular weight cutoff of the sample membrane is different from the porosity of the filter, fritte, membrane or any other material used to keep the matrix in the column.

8. A spin column, as in claim 1, where the column has one or more membranes.

9. A spin column as in claim 1, wherein the sample can move through the spin column by using a method selected from the group consisting of centrifugation, pressure and vacuum.

10. A Spin column as in claim 1, further comprising at least one additional spin column attached to said spin column series or in another combination.

11. An apparatus comprising: two or more micro spin columns, which can be joined in series with the following components:

A solid matrix, b. luer fittings at one or both ends of the column, and c. a porous filter, fritte, membrane or any other material used to keep the matrix in the column during centrifugation or vacuum application, d. a sample membrane located above the solid matrix, wherein the sample membrane is a dialysis membrane, and a collecting tube, which collects the sample after it has moved through the columns, wherein the collecting tube is a centrifuge tube and further comprising a centrifuge holding the centrifuge tube and columns.

12. An apparatus, as in claim 1 or 11, in which the fitting ends consist of:

a. one male luer and one female luer fitting, or b. two male luer fittings, or c. two female luer fittings, or d. one male luer fitting, or e. one female luer fitting.

13. An apparatus as in claim 1 or 11, wherein a male fitting on the spin column or the at least one additional spin column is slipped into a female fitting on the at least one additional spin column or the spin column, respectively, to create a joint.

14. An apparatus as in claim 13, wherein a male fitting on the spin column or the at least one additional spin column is screwed together with a female fitting on the at least one additional spin column or the spin column, respectively, to create a joint.

* * * * *